(12) United States Patent
Melvin et al.

(10) Patent No.: US 6,787,141 B1
(45) Date of Patent: Sep. 7, 2004

(54) PEPTIDE HAVING FOR FIBRINOGEN FRAGMENT E ACTIVITY, ANALOGS, ANTIBODIES AND USES THEREOF

(75) Inventors: William Thomas Melvin, Aberdeen (GB); William Douglas Thompson, Aberdeen (GB); Christina Maureen Stirk, Aberdeen (GB)

(73) Assignee: The University Court of The University of Aberdeen, Aberdeen (GB)

( * ) Notice: Subject to any disclaimer, the term of this patent is extended or adjusted under 35 U.S.C. 154(b) by 0 days.

(21) Appl. No.: 10/009,049

(22) PCT Filed: Jun. 7, 2000

(86) PCT No.: PCT/GB00/02197

§ 371 (c)(1),
(2), (4) Date: Apr. 1, 2002

(87) PCT Pub. No.: WO00/75175

PCT Pub. Date: Dec. 14, 2000

(30) Foreign Application Priority Data

Jun. 7, 1999 (GB) .............................................. 9912994

(51) Int. Cl.[7] ........................ A61K 39/00; A61K 38/00; C07K 7/00
(52) U.S. Cl. ........................ 424/185.1; 530/326; 514/14
(58) Field of Search ....................... 530/326; 424/185.1, 424/192.1; 514/2, 14

(56) References Cited

FOREIGN PATENT DOCUMENTS

| DE | 0 605 797 A | * | 7/1994 |
| WO | Wo98/54208 | * | 12/1998 |

OTHER PUBLICATIONS

Kogan TP, et al. A single amino acid residue can determine the ligand specificity of E–selectin. J Biol chem. 270(23):14047–5 1995.*

Ding L et al. Inhibition of cell migration and angiogenesis by the amino–terminal fragment of 24kD basic fibroblast growth facto J Biol Chem. 277(34):31056–61, 2002.*

Burgess WH et al. Possible dissociation of the heparin–binding and mitogenic activities of heparin–binding (acidic fibroblast) growth factor–1 from its receptor–binding activities by site–directed mutagenesis of a single lysine residue. J Cell Biol. 111(.*

Lazar E, et al. Transforming growth factor alpha: mutation of aspartic acid 47 and leucine 48 results in different biological activities. Mol Cell Biol. 8(3):1247–52, 1988.*

Bowie JU, et al. Deciphering the message in protein sequences: tolerance to amino acid substitutions. Science. 247(4948):1306–10, 1990.*

Stirk et al. Presence of growth–stimulating fibrin degradation products containing fragment E in human atherosclerotic plaques. Atherosclerosis. 1993 Nov.;103(2):159–69.*

Thompson et al. Angiogenic activity of fibrin degradation products is located in fibrin fragment E. J Pathol. 1992 Sep;168(1):47 53.*

* cited by examiner

*Primary Examiner*—Christina Chan
*Assistant Examiner*—Maher Haddad
(74) *Attorney, Agent, or Firm*—Dann, Dorfman, Herrell & Skillman, P.C.

(57) ABSTRACT

Fibrin degradation products stimulate cell proliferation and angiogenesis. The present invention provides peptides, analogs, and antibodies which are useful in the modulation of binding fibrin fragment E to cell receptors and the modulation of such activity.

3 Claims, 3 Drawing Sheets

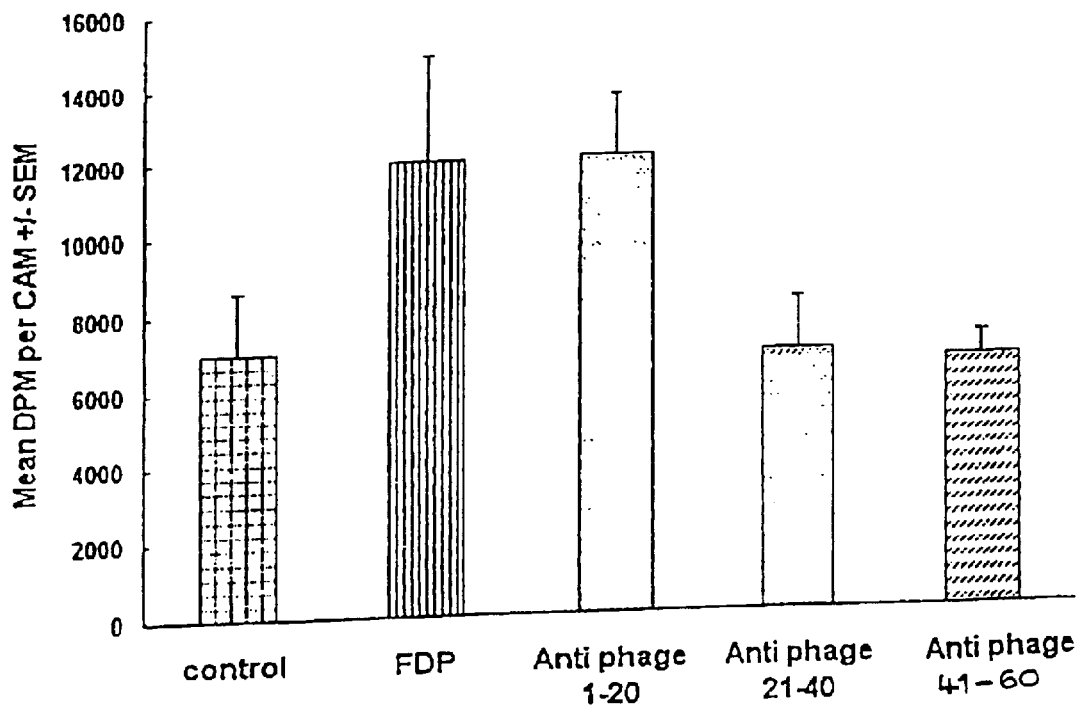
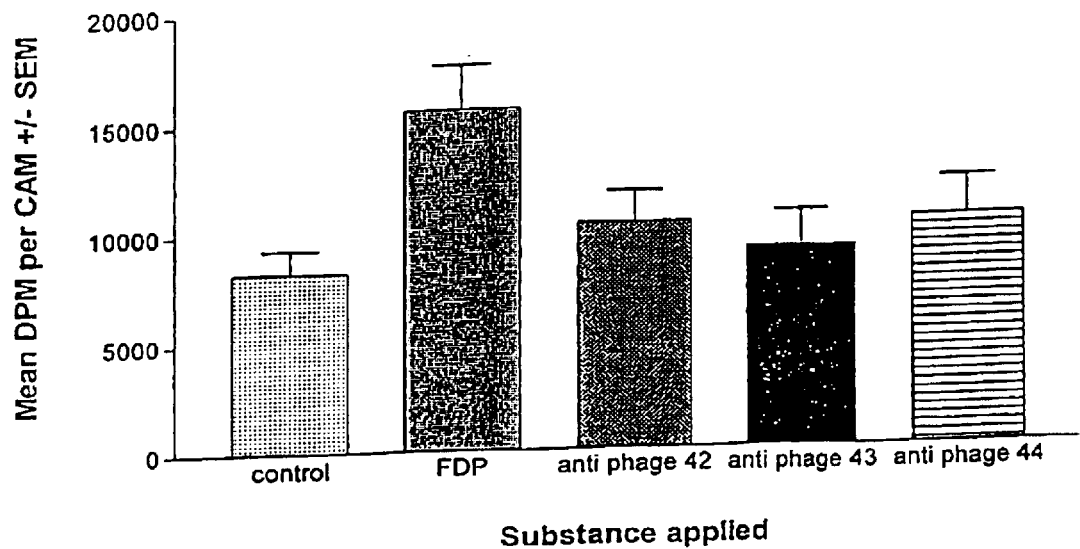

SEQUENCE LISTING

<160> NUMBER OF SEQ ID NOS: 6

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Derived
      from gene VIII phage library

<400> SEQUENCE: 1

Cys Arg Ala His Ser Phe Gly Ser Pro Arg Pro Leu Pro Val Val
 1               5                  10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Derived
      from gene VIII phage library

<400> SEQUENCE: 2

Ser Arg Ala His Ser Phe Gly Ser Pro Arg Pro Leu Pro Val Val
 1               5                  10                  15

```
<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Derived
      from gene VIII phage library

<400> SEQUENCE: 3

Cys Arg Ala His Ser Phe Val Ser Pro Arg Pro Leu Pro Val Val
  1               5                  10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Derived
      from gene VIII phage library

<400> SEQUENCE: 4

Gln Pro Asp Pro His Leu Met Met Trp Lys Leu Pro Gly Phe Pro
  1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Derived
      from gene VIII phage library

<400> SEQUENCE: 5

Ala Leu Ser Lys Arg Pro Val Gly Arg Pro Arg Val Cys Thr Gly
  1               5                  10                  15

<210> SEQ ID NO 6
<211> LENGTH: 16
<212> TYPE: PRT
<213> ORGANISM: Drosophila melanogaster

<400> SEQUENCE: 6

Arg Gln Ile Lys Ile Trp Phe Gln Asn Arg Arg Met Lys Trp Lys Lys
  1               5                  10                  15
```

PEPTIDE HAVING FOR FIBRINOGEN FRAGMENT E ACTIVITY, ANALOGS, ANTIBODIES AND USES THEREOF

FIELD OF THE INVENTION

The present invention relates broadly to compounds which act as modulators or mimics of fibrin fragment E and their use.

Basic Pathology of Chronic Inflammation, Healing and Repair

Fibrinogen is the major circulating plasma protein involved in blood clot formation. Activation of the clotting enzyme cascade, by for example injury or inflammation, results in conversion of prothrombin to thrombin which cleaves two small fibrinopeptides (A and B) from each soluble fibrinogen molecule to give fibrin monomer. Cross linkage of monomers is the final step of the coagulation system that gives solid fibrin. Whole blood includes platelets and forms blood clot in wounds, and is termed thrombus when in abnormal arteries and veins: inflammatory exudate is platelet free and forms fibrin alone.

Fibrin deposition and degradation is a major feature of the pathology of acute and chronic inflammation at any site in the body regardless of the underlying disease aetiology. This process is apparent at the histological level in the healing wound, the organising thrombus, the advanced atherosclerotic plaque, and many other types of pathological lesions including the growing edge of some types of cancer. The fibrin mesh provides a provisional matrix for cell ingrowth, being progressively invaded in wound healing by inflammatory cells (macrophages), new small blood vessels (capillary buds), connective tissue cells (fibroblasts) and the epidermis (squamous epithelium). In the context of the large arteries subject to atherosclerosis, the endothelium of the luminal surface and the smooth muscle cells of the vascular wall invade the fibrin mesh. Secretion of plasminogen activator is the common factor that provides controlled lysis of the fibrin substratum via plasmin degradation, releasing fibrin degradation products. Fibrin degradation products are composed of combinations of two moieties termed fragments D and E. Eventually the fibrin present is replaced by new cells and matrix forming new tissue. These basic features apply to many types of human and animal disease.

Fibrin Degradation Products

Although fibrin may be a factor common to many pathologies involving cell proliferation, it has generally been assumed that its main function was to provide an inert physical matrix to support cell movement. However there has been evidence for some time that fibrinopeptides and fibrin degradation products have biological activity particularly as soluble mediators of chemotaxis, the phenomenon of directional cell movement (1). It has been proposed that fibrin degradation products were a major pathological growth factor common to all sites of chronic inflammation. Using the chick chorioallantoic membrane as an in vivo test model for detection of angiogenic growth factors it has been suggested that fibrin degradation products were angiogenic (2), had stimulatory effects on collagen synthesis (3), and that specifically fibrin fragment E may be the active component (4).

Fibrin deposition and lysis is believed to be relevant to a wide spectrum of human diseases including vascular restenosis, cancer, atherogenesis, rheumatoid arthritis, diabetes and renal diseases.

U.S. Pat. No. 5,981,697 describes generation of antibodies which bind fibrinogen fragments E1, E2 and E3. Bach et al (1998) J Biol Chem 273 pp30719–30728 describes an interaction of the fibrinogen β15–42 sequence with endothelial cell VE-cadherin. Lee et al (1999), Molecules and Cells 9(1) 7–13 describes the stimulation of production of IL-6 in macrophages by fragment E of fibrin and fibrinogen.

SUMMARY OF THE INVENTION

The production of antibodies to fibrin fragment E has been previously described, the antibodies being derived using an Fd phage combinatorial library of random epitope display to select clones binding and common to both polyclonal rat and rabbit anti E blocking antisera (32). In the present invention, the inventors have individualised a number of compounds which modulate the induction of cell proliferation induced by fibrin degradation products. The present inventors have further demonstrated that fibrin fragment E binds to a cell membrane component of approximately 66 kDa in size using, for example, ligand blotting of SDS-PAGE gels of cell membranes from chick fibroblasts. The presence of a specific binding site for fragment E raises the possibility that agonists and antagonists of its binding could be used to modulate its binding and thus modulate its effects. Such effects include induction of cell proliferation, angiogenesis, fibrogenesis and collagen synthesis. Such agonists and antagonists, such as those disclosed herein, may also have modulatory effects on, for example, cell stimulation per se. Such modulation may be very useful in the control of cell proliferation seen in atherosclerosis, and particularly in post angioplasty restenosis. Using the techniques described below, the inventors have identified a number of compounds which modulate the FDP induced stimulation of cell proliferation. Preferably the variant retains fibrin fragment E activity.

Accordingly, the present invention provides a peptide comprising a sequence selected from the group consisting of:

CRAHSFGSPRPLPVV (SEQ ID NO:1)
SRAHSFGSPRPLPVV (SEQ ID NO:2)
CRAHSFVSPRPLPVV (SEQ ID NO:3)
QPDPHLMMWKLPGFP (SEQ ID NO:4)

or a fragment thereof capable of modulating fibrin fragment E activity.

As described above, fibrin fragment E activity refers to at least one of following activities: induction of cell proliferation, angiogenesis, fibrogenesis and collagen synthesis.

In a further aspect of the invention, there is provided a functional variant of the above peptide, which variant comprises from one to four, preferably from one to three, more preferably one or two, amino acid variations, including substitutions, insertions and deletions. Preferably, the variant retains the capability of modulating fibrin fragment E activity.

In another aspect of the invention there is provided a fusion peptide which comprises a first portion having the amino acid sequence of a peptide according to the invention as defined above and a second portion, attached to the N- or C-terminus of the first portion, which comprises a sequence of amino acid not naturally contiguous to the first portion. Such heterologous peptide fusions are also referred to herein as peptides of the invention.

In a further aspect, the invention provides assay methods for the identification of substances which bind to or modulate the activity of peptides of the invention, either in monomeric or oligomeric form.

In a further aspect of the invention, "analogs" of the peptides of the invention are provided. Analogs are non-peptide compounds which share fibrin fragment E activity, for example the ability to competitively inhibit binding of FDPs for example, fibrin fragment E to the fragment E receptor. Analogs are a further aspect of the invention inasmuch as they are novel. Analogs may be produced by any of the techniques described herein or may be derived using, for example, combinatorial chemical libraries known in the art. Examples of such libraries are reviewed in Newton G R, Exp. Opin. Ther. Patents (1997) 7(10): 1183–1194. Where the term "chemical library" is used herein, those skilled in the art will understand its meaning accordingly.

The invention also provides antibodies and binding fragments thereof capable of selectively binding to peptides or analogs of the invention.

In a further aspect, the invention provides a pharmaceutical composition comprising a peptide, analog or antibody according to the invention together with a pharmaceutically acceptable carrier or diluent.

Peptides, analogs or antibodies and compositions of the invention may be used for a number of purposes. They are also useful as research agents to investigate the receptor for fibrin fragment E and the activation of cell proliferation by fibrin degradation products. They may also be useful in modulating fibrin fragment E activity such as cell proliferation, particularly inhibition of angiogenesis.

Thus in a preferred aspect the peptides, analogs or antibodies of the invention may be used in a method of modulating fibrin fragment E activity, said method comprising introducing an effective amount of a peptide of the invention. The method may be practised in vitro or in vivo. Where it is practised in vivo the invention will find use in a method of treatment of the human or animal body, particularly in methods of treating cancer or other proliferative diseases, including restenosis, e.g. caused by regrowth of vascular cells following angioplasty procedures.

DETAILED DESCRIPTION OF THE INVENTION

Peptides

"Peptides" of the invention should be understood to include fragments thereof and variants of said sequences and fragments as set out above, as well as heterologous fusions of said peptides.

The term "comprising" means "including" and allows for the presence of further amino acid sequences, or other chemical moieties, at the—and/or C-termini, provided that the peptide as a whole retains the ability to bind to a fibrin fragment E binding site.

It is preferred that peptides of the invention (including fragments of SEQ ID NOs 1–4 above and other sequences of the invention described herein), excluding any heterologous fusion sequence, are from 3 to 15, such as from 5 to 15, e.g. 5 to 8, 5 to 10, 8 to 15 or 8 to 11 amino acids in length.

The presence of a heterologous fusion sequence, which in itself has no activity in binding to the fibrin fragment E binding site will vary according to its intended function. Such functions include the ability to translocate across membranes, an epitope function to allow for purification or identification of the peptide, and the like. As a rough guide, the heterologous fusion sequence will be from 4 to 500, such as from 4 to 100 or 10 to 50, e.g from 10 to 30 amino acids in size.

The second peptide portion can be any sequence selected by those of skill in the art taking into account the intended purpose of the fusion. For example, the second portion may comprise a detectable tag such as a T7 tag, HA tag or a myc tag allowing identification of the peptide in a cell and/or its recovery. The second portion may also be a signal sequence directing expression of the peptide from a host cell in which the fusion is being expressed. This will be useful for the recombinant production of peptides of the invention.

The second portion may also comprise a molecular tag which influences the overall structure. A number of helix initiators which aid the formation of α-helixes which comprise short peptide sequences are known in the art.

In a preferred embodiment the second peptide portion is a membrane translocation sequence, capable of directing a peptide through the membrane of a eukaryotic cell. Example of such peptides include the HSV-1 VP22 protein (Elliot et al, 1997), the HIV Tat protein (for example residues 1–72, 37–72 or 48–60; Fawell et al, 1994) or a sequence that is derived from the *Drosophila melanogaster* antennapedia protein, e.g. the 16 amino acid peptide sequence:

Arg-Gln-Ile-Lys-Ile-Trp-Phe-Gln-Asn-Arg-Arg-Met-Lys-Trp-Lys-Lys (SEQ ID NO: 6).

A translocation peptide may be at the N-terminus or the C-terminus of the heterologous fusion. Unless the context requires otherwise, reference below to peptides of the invention includes the fusion peptides described above.

Variant Peptides

Certain amino acid residues of peptides 1–4 above may be substituted without significant loss of the ability of the peptide to bind to the fibrin fragment E binding site. Thus, amino acids of these peptides may be substituted to provide variant peptides which form a further aspect of the invention, within the above-described ranges.

Substitutions may include conserved substitutions, for example according to the following table, where amino acids on the same block in the second column and preferably in the same line in the third column may be substituted for each other:

| ALIPHATIC | Non-polar | G | A | P | |
| | | I | L | V | |
| | Polar - uncharged | C | S | T | M |
| | | N | Q | | |
| | Polar - charged | D | E | | |
| | | K | R | H | |
| AROMATIC | | F | W | Y | |

Alternatively, any amino acid may be replaced by a small aliphatic amino acid, preferably glycine or alanine.

In addition, deletions and insertions may also be made. Insertions are preferably insertions of small aliphatic amino acids, such as glycine or alanine, although other insertions are not excluded.

Variant peptides may also be modified in any of the ways described herein for peptides of the invention. This includes for example "reverse" C-terminal to N-terminal sequences, synthetic amino acids, modified side chains and labelling.

Where methods for the production and use of peptides of the invention are described, it will be understood that reference is also being made to variant peptides of the invention unless the context explicitly indicates otherwise.

In another aspect, a peptide of the invention may be provided in the form of molecules which contain multiple copies of the peptide (or mixtures of peptides of the invention). For example, the amino group of the side chain of lysine may be used as an attachment point for the carboxy terminus of an amino acid. Thus two amino acids may be joined to lysine via carbonyl linkages, leading to a branched structure which may in turn be branched one or more times. By way of example, four copies of a peptide of the invention may be joined to such a multiple antigen peptide (MAP), such as a MAP of the structure $Pep_4$-$Lys_2$-Lys-X, where Pep is a peptide of the invention (optionally in the form of a heterologous fusion), Lys is lysine and X is a terminal group such as β-alanine which provides for joining of the MAP core to a solid support such as a resin for synthesis of the Pep$_4$-MAP peptide and which may be removed from the support once synthesis is complete.

Linear multimers of peptides of the invention may also be provided.

Other multiple peptide structures may be obtained using the MAP cores described in: Lu et al, 1991, Mol Immunol, 28, 623–30; Briand et al, 1992, J Immunol Methods, 156, 225–65; Ahlborg, 1995, J Immunol Methods, 179, 269–75.

A multimer of peptides of the present invention may be fused to a translocation peptide for directing it through the membrane of a eukaryotic cell, as discussed herein. A tranalocation peptide may be fused to an N-terminus or a C-terminus of the multimer, or it may be incorporated at an intermediate position within the multimer.

Where multimers of the invention are provided, they may comprise different peptides of the invention or be miltimers of the same peptide.

Production and Modification of Peptides

Except where specified to the contrary, the peptide sequences described herein are shown in the conventional 1-letter code and in the N-terminal to C-terminal orientation. The amino acid sequence of peptides of the invention may also be modified to include non-naturally-occurring amino acids or to increase the stability of the compound in vivo. When the compounds are produced by synthetic means, such amino acids may be introduced during production. The compound may also be modified following either synthetic or recombinant production.

Peptides of the invention may be made synthetically or recombinantly, using techniques which are widely available in the art. Synthetic production generally involves step-wise addition of individual amino acid residues to a reaction vessel in which a peptide of a desired sequence is being made.

Peptides of the invention may also be made synthetically using D-amino acids. In such cases, the amino acids will be linked in a reverse sequence in the C to N orientation. This is conventional in the art for producing such peptides.

A number of side-chain modifications for amino acids are known in the art and may be made to the side chains of peptides of the present invention. Such modifications include for example, modifications of amino groups by reductive alkylation by reaction with an aldehyde followed by reduction with NaBH$_4$, amidination with methylacetimidate or acylation with acetic anhydride.

The guanidino groups of arginine residues may be modified by the formation of heterocyclic condensation products with reagents such as 2,3-butanedione or glyoxal. Sulphydryl groups may be modified by methods such as carboxymethylation, tryptophan residues may be modified by oxidation or alkylation of the indole ring and the imidazole ring of histidine residues may be modified by alkylation.

The carboxy terminus and any other carboxy side chains may be blocked in the form of an ester group, e.g. a $C_{1-6}$alkyl ester.

The above examples of modifications to amino acids are not exhaustive. Those of skill in the art may modify amino acid side chains where desired using chemistry known per se in the art.

Expression Vectors, Nucleic Acids and Host Cells

In another aspect, the invention provides nucleic acids encoding peptides of the invention. For example, the nucleic acid may be a nucleic acid primer consisting essentially of between about 15 to 50 nucleotides. Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below in connection with expression vectors.

Preferably, a polynucleotide of the invention in a vector is operably linked to a control sequence which in capable of providing for the expression of the coding sequence by the host cell, i.e. the vector is an expression vector.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Such vectors may be transformed into a suitable host cell to provide for expression of a peptide of the invention. Thus, in a further aspect the invention provides a process for preparing peptides according to the invention which comprises cultivating a host cell transformed or transfected with an expression vector as described above under conditions to provide for expression by the vector of a coding sequence encoding the peptides, and recovering the expressed peptides.

The vectors may be for example, plasmid, virus or phage vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used in vitro, for example for the production of RNA or used to transfect or transform a host cell.

A further embodiment of the invention provides host cells transformed or transfected with the vectors for the replication and expression of polynucleotides of the invention. The cells will be chosen to be compatible with the said vector and may for example be bacterial, yeast, insect or mammalian.

Promoters and other expression regulation signals may be selected to be compatible with the host cell for which the expression vector is designed. For example, yeast promoters include *S. cerevisiae* GAL4 and ADH promoters, *S. pombe* nmt1 and adh promoter. Mammalian promoters include the metallothionein promoter which is can be included in response to heavy metals such as cadmium. Viral promoters include the SV40 large T antigen promoter, retroviral LTR promoters and adenovirus promoters. All these promoters are readily available in the art.

The vector may also be adapted to be used in vivo, for example in a method of therapy. Vectors suitable for use in therapy include adenoviral vectors, retroviral vectors and alphavirus vectors. Such vectors are adapted for use in therapy by a number of modifications, for example by making the vector replication defective. Reference may be made to, for example, WO95/14091 for a description of retroviral vectors and WO95/07994 for a description of alphavirus vectors. The disclosures of both references are hereby incorporated by reference.

Vectors for use in therapy will generally be administered in the form of packed viral particles containing the vector, the particles being delivered to the site of fibrin fragment E activity, for example a tumour or other proliferating cells.

Vectors for production of peptides of the invention or for use in gene therapy include vectors which carry a mini-gene sequence of the invention.

For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Antibodies

A peptide or analog according to the present invention may be used as an immunogen or otherwise in obtaining specific antibodies. Antibodies are useful in purification and other manipulation of peptides or analogs, diagnostic screening and therapeutic contexts. This is discussed further below.

The provision of the peptides or analogs of the invention also enables for the production of antibodies which may bind the portion of fibrin fragment E which interacts with its receptor in a specific manner. Thus the invention provides an antibody which is able to bind specifically to a peptide or analog of the invention or such portion. Such antibodies may be produced using epitopes of peptides or analogs of the invention.

Another feature of the present invention is the generation of anti-fragment E antibodies which prevent the binding of the fibrin fragment E to its receptor. Polyclonal antibodies which block the cell proliferative activity of fibrin fragment E can be raised by injection of the whole fragment E in rabbits. When admixed with fibrin degradation products the cell proliferative activity is abolished (17).

For instance, purified peptides of the invention, or a variant thereof, e.g. produced recombinantly by expression from encoding nucleic acid therefor, may be used to raise antibodies employing techniques which are standard in the art. Antibodies and peptides or analogs comprising antigen-binding fragments of antibodies may be used as discussed further below.

Methods of producing antibodies include immunising a mammal (e.g. human, mouse, rat, rabbit, horse, goat, sheep or monkey) with the protein or a fragment thereof. Antibodies may be obtained from immunised animals using any of a variety of techniques known in the art, and might be screened, preferably using binding of antibody to antigen of interest (which may be labelled). This is discussed below.

For instance, Western blotting techniques or immunoprecipitation may be used (Armitage et al, 1992, Nature 357: 80–82). Antibodies may be polyclonal or monoclonal.

Modification of Antibodies

Antibodies may be modified in a number of ways. Indeed the term "antibody" should be construed as covering any specific binding substance having a binding domain with the required specificity. Thus, this term covers antibody fragments, derivatives, functional equivalents and homologues of antibodies, including any peptide comprising an immunoglobulin binding domain, whether natural or synthetic. Chimaeric molecules comprising an immunoglobulin binding domain, or equivalent, fused to another peptide are therefore included. Cloning and expression of Chimaeric antibodies are described in EP-A-0120694 and EP-A-0125023. It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the Vl and VH domains of a single antibody; (iv) the dAb fragment (Ward, E. S. et al., Nature 341, 544–546 (1989) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423–426, 1968; Huston et al, PNAS USA, 85, 5879–5883, 1988); (viii) bispecific single chain Fv dimers (PCT/US92/09965) and (ix) "diabodies", multivalent or multispecific fragments constructed by gene fusion (WO94/13804; P Holliger et al Proc. Natl. Acad. Sci. USA 90 6444–6448, 1993).

Diabodies are multimers of peptides, each peptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one peptide within the multimer with the second domain of another peptide within the multimer (WO94/13804).

As an alternative or supplement to immunising a mammal, antibodies with appropriate binding specificity may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

Binding of Peptides and Analogs to Antibodies

Immunoassays for detecting antibodies are well known in the art and will generally comprise:

(a) providing a peptide comprising an epitope bindable by an antibody against said protein;

(b) incubating a biological sample with said peptide under conditions which allow for the formation of an antibody-antigen complex; and (c) determining whether antibody-antigen complex comprising said peptide is formed.

A peptide or analog of the invention may be labelled with a revealing label. The revealing label may be any suitable label which allows the peptide or analog to be detected. Suitable labels include radioisotopes, e.g. $^{125}$I, enzymes, antibodies, polynucleotides and linkers such as biotin. Labelled peptides or analogs of the invention may be used in diagnostic procedures such as immunoassays in order to determine the amount of a peptide or analog of the invention in a sample. Peptides or analogs or labelled peptides or analogs of the invention may also be used in serological or cell mediated immune assays for the detection of immune reactivity to said peptides or analogs in animals and humans using standard protocols.

A peptide or analog or labelled peptide or analog of the invention or fragment thereof may also be fixed to a solid phase, for example the surface of an immunoassay well or dipstick.

Such labelled and/or immobilized peptides or analogs may be packaged into kits in a suitable container along with suitable reagents, controls, instructions and the like.

Such peptides or analogs and kits may be used in methods of detection of antibodies to such peptides or analogs present in a sample or active portions or fragments thereof by immunoassay.

Uses of Antibodies

Antibodies raised to a peptide can be used in the identification and/or isolation of variant peptides, and then their encoding genes. Thus, the present invention provides a method of identifying or isolating a fibrin degradation product binding epitope or variant thereof (as discussed above), comprising screening candidate peptides with a peptide comprising the antigen-binding domain of an antibody (for example whole antibody or a fragment thereof) which is able to bind said fibrin degradation product binding epitope peptide or variant thereof, or preferably has binding specificity for such a peptide. Specific binding members such as antibodies and peptides comprising antigen binding domains of antibodies that bind and are preferably specific for a fibrin degradation product binding epitope peptide or mutant or derivative thereof represent further aspects of the present invention, as do their use and methods which employ them.

Candidate peptides for screening may for instance be the products of an expression library created using nucleic acid derived from an animal of interest, or may be the product of a purification process from a natural source. Analogs may be produced by any of the techniques described herein or may be derived using, for example, combinatorial chemical libraries known in the art. Examples of such libraries are reviewed in Newton G R, Exp. Opin. Ther. Patents (1997) 7(10): 1183–1194.

A peptide found to bind the antibody may be isolated and then may be subject to amino acid sequencing. Any suitable technique may be used to sequence the peptide either wholly or partially (for instance a fragment of the peptide may be sequenced). Amino acid sequence information may be used in obtaining nucleic acid encoding the peptide, for instance by designing one or more oligonucleotides (e.g. a degenerate pool of oligonucleotides) for use as probes or primers in hybridization to candidate nucleic acid, or by searching computer sequence databases, as discussed further below.

The reactivities of antibodies with a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

The mode of determining binding is not a feature of the present invention and those skilled in the art are able to choose a suitable mode according to their preference and general knowledge.

Antibodies according to the present invention may be used in screening for the presence of a peptide or analog, for example in a test sample containing cells or cell lysate as discussed, and may be used in purifying and/or isolating a peptide or analog according to the present invention, for instance following production of the peptide by expression from encoding nucleic acid therefor.

Antibodies may modulate the activity of the peptide or analog to which they bind and so, if that peptide or analog has a deleterious effect in an individual, may be useful in a therapeutic context (which may include prophylaxis).

An antibody may be provided in a kit, which may include instructions for use of the antibody, e.g. in determining the presence of a particular substance in a test sample. One or more other reagents may be included, such as labelling molecules, buffer solutions, elutants and so on. Reagents may be provided within containers which protect them from the external environment, such as a sealed vial.

Development of Mimetics

A peptide, analog or antibody according to the present invention may be used in screening for molecules which bind to it or modulate its activity or function. Such molecules may be useful in a therapeutic (possibly including prophylactic) context.

The stimulation of cell proliferation induced by fibrin degradation products, for example fibrin fragment E, provides a target for the development of therapeutic agents capable of inhibiting uncontrolled cell proliferation, for example found in restenosis or in tumour cells.

A number of assay formats are described in WO94/10307 and WO96/10425. The provision of the peptides, analogs or antibodies of the invention provide positive control reagents for such assays which will be desirable in the design of high throughput screening assays for novel compounds which can exert a similar effect. The peptides, analogs or antibodies of the invention further provide a basis for rational drug design of pharmaceutical compounds to target the fibrin fragment E binding site.

Peptides, analogs or antibodies of the present invention may be used to develop mimetics. This might be desirable where the peptide, analog or antibody is difficult or expensive to synthesise or where it is unsuitable for a particular method of administration, e.g. peptides may be unsuitable active agents for oral compositions as they may be quickly degraded by proteases in the alimentary canal. Mimetic design, synthesis and testing may be used to avoid randomly screening large numbers of peptides or analogs for a target property.

There are several steps commonly taken in the design of a mimetic from a peptide, analog or antibody having a given target property. Firstly, the particular parts of the peptide, analog or antibody that are critical and/or important in determining the target property are determined. In the case of a peptide, this can be done by systematically varying the amino acid residues in the peptide, e.g. by substituting each residue in turn. These parts or residues constituting the active region of the peptide are known as its "pharmacophore".

Once the pharmacophore has been found, its structure is modelled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process. A template molecule is then selected onto which chemical groups which mimic the pharmacophore can be grafted. The template molecule and the chemical groups grafted on to it may conveniently be selected so that the mimetic is easy to synthesise, is likely to be pharmacologically acceptable, and does not degrade in vivo, while retaining the biological activity of the lead peptide, analog or antibody. Alternatively, the pharmacophore can be used to form the basis of a search of a computer database of structures to identify a mimetic. The mimetic or mimetics found by any approach described herein can then be screened to see whether they have the target property, or to what extent they exhibit it. Further optimisation and/or modification can then be carried out to arrive at one or more final mimetics for in vivo or clinical testing.

Mimetics obtainable by the above and other methods available in the art form a further aspect of the present invention.

Compositions

Peptides, analogs or antibodies of the invention may be in a substantially isolated form. It will be understood that the peptide, analog or antibody may be mixed with carriers or diluents which will not interfere with the intended purpose of the peptide, analog or antibody and still be regarded as substantially isolated. A peptide, analog or antibody of the invention may also be in a substantially purified form, in which case it will generally comprise the peptide, analog or antibody in a preparation in which more than 90%, e.g. 95%, 98% or 99% of the peptide, analog or antibody in the preparation is a peptide, analog or antibody of the invention.

Peptides or analogs of the invention may be formulated in the form of a salt. Salts of peptides or analogs of the invention which may be conveniently used in therapy include physiologically acceptable base salts, eg derived from an appropriate base, such as alkali metal (e.g. sodium), alkaline earth metal (e.g. magnesium) salts, ammonium and $NR_4$ (wherein R is $C_{1-4}$ alkyl) salts. Salts also include physiologically acceptable acid addition salts, including the hydrochloride and acetate salts.

Peptides, including fusion peptides, analogs, or antibodies of the invention may be formulated into pharmaceutical compositions. The compositions comprise the peptide, analog or antibody together with a pharmaceutically acceptable carrier or diluent. Pharmaceutically acceptable carriers or diluents include those used in formulations suitable for oral, topical, or parenteral (e.g. intramuscular or intravenous) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For example, formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the peptide, analog or antibody to blood components or one or more organs.

Suitable liposomes include, for example, those comprising the positively charged lipid (N[1-(2,3-dioleyloxy) propyl]-N,N,N-triethylammonium (DOTMA), those comprising dioleoyl-phosphatidylethanolamine (DOPE), and those comprising 3β[N-(n',N'-dimethylaminoethane)-carbamoyl]cholesterol (DC-Chol).

Compositions may comprise any desired amount of a peptide, analog or antibody of the invention. In part this will depend upon the intended formulation and its intended use. By way of general guidance the composition may comprise from about 1% to about 99%, for example from 10% to 90% of a peptide, analog or antibody of the invention.

The composition may comprise a mixture of more than one, for example two or three, peptides, analogs or antibodies of the invention.

Peptides, analogs or antibodies of the invention may also be used in conjunction with a second agent capable of inhibiting cell proliferation, in order to provide a combined anti-proliferative effect. Thus the composition may also comprise other pharmaceutically active ingredients, in particular cytotoxic and/or cytostatic agents.

Alternatively, a pepptide, amalog or antibody of the invention may be delivered to a patient in a separate composition from a cytotoxic or cytostatic agent but simultaneously or sequentially. "Sequentially" means that one of the peptides, analogs or antibodies or the agent will be delivered first, and the other delivered within a period of time such that the enhanced effect of the two agents together is achieved in a target proliferating cell. Where one or both agents is delivered over a period of time, e.g. through intravenous infusion, the time period of administration of the agents may be sequential or overlapping.

When used in methods of treatment of the human or animal body, the peptide, analog or antibody and the agent may be administered to a subject at the same site or at different sites.

Thus the invention provides a peptide, analog or antibody of the invention and a cytotoxic or cytostatic agent for separate or simultaneous use in the treatment of proliferating cells, for example tumour cells, either in vitro or in vivo.

Where in vitro use is contemplated, this will include ex-vivo, e.g. in the treatment of bone marrow from a subject which may be reimplanted into the subject after treatment.

The invention further provides the use of a peptide, analog or antibody of the invention for the manufacture of a medicament for the treatment of proliferating cells wherein said cells are also treated, separately or simultaneously, with a cytotoxic or cytostatic agent.

Numerous cytotoxic and/or cytostatic agents are known in the art (e.g. listed in The Merck Index, 12th Edition, 1996) and include:

alkaloids such as etoposide and other toposiomerase inhibitors, paclitaxel, vinblastine and vincristine; alkylating agents such as alkyl sulphonates (e.g. busulfan), aziridines, ethylenimines and methylmelomines (e.g. triethylenemelamine and triethylenephosphoramide), nitrogen mustards (e.g. cyclophosphamide, melphalan and uracil mustard), nitrosoureas and the like;

antibiotics and analogues such as actinomycins, anthramycin, doxorubicin, puromycin and the like;

antimetabolites such as folic acid analogues (e.g. methotrexate), purine analogues (e.g. 6-mercaptopurine and thioguanine) and pyrimidine analogues (e.g fluorouracil);

platinum complexes such as cisplatin; and other anti-neoplastic compounds including for example hydroxyurea.

In addition, the cytotoxic or cytostatic compound may be an immunomodulatory compound or hormonal analogue compound. Examples of the former include interferons α, β and δ and interleukins such as IL-2. Examples of the latter include antiandrogens, antiestrogens (e.g. tamoxifen), aromatase inhibitors, estrogen analogues, LHRH analogues (e.g. buserelin) and the like.

Cytostatic compounds also include antimetastatic agents such as matrix metalloproteinase inhibitors such as batimastat.

Methods of Treatment

Peptides, analogs, or antibodies of the invention may also be used in methods of treating a number of diseases, in particular those diseases in which uncontrolled proliferation of cells may play a part. Conditions in which uncontrolled cell proliferation may be treated include vascular restenosis, cancer, atherogenesis, rheumatoid arthritis, diabetes and renal diseases and psoriasis.

Angiogenesis and Wound Healing

Fibrin deposition and lysis are essential features, as demonstrated by abnormalities of healing in the plasminogen and fibrinogen knockout mouse models (5, 6). The present inventors have shown in a mouse incised wound model that the peak of angiogenic activity in simple wound extracts occurs at day 3, preceding the peak of wound vascular density at day 5 (7) with the bulk of the angiogenic activity suggested to be attributable to fibrin fragment E (8). Compounds of the invention may therefore find use in treatments concerned with wound healing.

Vascular Restenosis

The likelihood of clinically significant post-angioplasty restenosis has been generally understood to be predicted to a fair extent by the amount of blood clot at the angioplasty site. The antithrombin drug hirudin has been partially successful in reducing restenosis experimentally and in man (9), but it has been unclear whether this is attributable to clot reduction or prevention of direct thrombin stimulation of smooth muscle cell proliferation via the PAR-1 thrombin receptor (10). However it is now apparent that the PAR-1 knockout mouse is normal and has near normal wound healing (11), and that intimal hyperplasia is not inhibited by an antisense thrombin receptor oligodeoxynucleotide following carotid injury in the rabbit (12). An alternative candidate that is both thrombin and plasmin dependant, but not thrombin receptor dependant is fibrin fragment E. Fibrin degradation products are abundant at sites of healing and repair, including sites of vascular injury and in extracts of proliferative types of human atherosclerotic plaque. The present inventors have shown that fibrin fragment E stimulates smooth muscle cell proliferation and outgrowth from aortic media explants in culture (13). This occurs in serum rich culture in which thrombin is inactive. The peptides, analogs and antibodies therefore find use in treatment and prevention of restenosis.

Atherogenesis

The link between abnormalities of the coagulation system and thrombosis of a coronary artery is well established not only in terms of the actual clot but in terms of risk of myocardial infarction in human populations. In many prospective studies, the plasma levels or activities of coagulation factors such as fibrinogen, factor VIIa and fibrin degradation products (D dimer assays) have been shown to be predictive risk factors for myocardial infarction, and other vascular events such as stroke and progressive peripheral vascular disease (14, 15, 16). A substantial proportion of the risk due to cigarette smoking is attributable to raised fibrinogen. The mode of interaction of this risk factor with the actual lesions of atherosclerosis, the atherosclerotic plaques within the artery wall, remains unexplained, but the end result, accumulation of fibrin admixed with the lipid core of the plaque and forming overlying thrombus in minor and major terminal events is well established.

The major pathogenic feature of atherogenesis is the response to fibrin and lipid accumulation by the smooth muscle cells of the arterial wall. Smooth muscle cell proliferation has long been recognised as the key event in plaque development, as it is in the more acute lesion of post angioplasty restenosis (17). Atherosclerotic lesions can be divided into several types, the earliest thought to be the gelatinous lesions, the precursors of the fibrous plaques. The early gelatinous lesions contain little lipid but significant amounts of fibrin related antigens (FRA) (18). In the more advanced lesions, fibrin is deposited in layers suggesting repeated thrombotic episodes (19). In all lesions the FRA are largely derived from cross-linked fibrin not fibrinogen suggesting continuous deposition and lysis of fibrin (20).

Soluble extracts of intima from active types of lesions from human autopsy and surgical material have been shown by the present inventors to stimulate cell proliferation in the in vivo chick chorioallantoic membrane test model(21). This work was extended to show that for a short series of stimulatory extracts, the bulk of the activity was removed by passing each through an affinity column containing antifibrin(ogen) antibody (22). Selective removal was again achieved with a bound specific anti fragment E antibody, but not with a bound anti fragment D antibody.

Rheumatoid Arthritis

Rheumatoid arthritis is of unknown cause but is known to be driven by the immune system. This causes episodic inflammation of the synovial lining of the joint, with deposition of fibrin which becomes organised by fibrovascular ingrowth, termed pannus, forming a membrane rich in inflammatory cells. This extends over the joint cartilage, releasing proteolytic enzymes that digest and gradually destroy the joint surface causing pain and immobility. Anti inflammatory drugs help symptoms but do not arrest disease progress significantly. Prevention of pannus extension during acute episodes may well be advantageous.

Diabetic Retinopathy

Diabetic retinopathy is due to narrowing of the microvascular blood supply vessels within the eye as elsewhere in the body in poorly controlled diabetes mellitus. It is characterised by proliferation of leaky new blood vessels in response to ischaemic areas of retina. The combination of fibrovascular proliferation and contraction involves the vitreous and distorts and destroys the retina. Fibrin deposition and degradation are likely to contribute to this disadvantageous instance of normal healing and repair.

Renal Disease: Acute and focal glomerulonephritis are characterised by deposition of both immune complexes and fibrin in the glomerulus with associated inflammatory cells. There is resultant cellular proliferation leading to glomerulosclerosis and permanent loss of function with renal failure in many cases. Anti-inflammatory drugs could be supplemented with the agents to inhibit cell proliferation.

Tumour Growth and Metastasis

For a malignant, invasive epithelial tumour of any type to grow more than 1mm and invade surrounding normal tissues, there is an absolute requirement for recruitment of a new blood supply. This phenomenon of tumour angiogenesis provides a target for therapeutic anti cancer intervention. These new small capillary vessels are leaky, and plasma proteins including fibrinogen are abundant in adjacent connective tissue at the tumour edge. Although it was once believed that fibrin was deposited at the moving edge of stroma surrounding most invasive tumours as in a wound (23), it is now believed that many tumour types do not display a complete set of procoagulant factors for this to happen. However there are two major exceptions, oat cell carcinoma of lung and clear cell carcinoma of kidney (24, 25). These two tumour types are common, are extremely vascular, show fibrin deposition, and are hard to treat once spread by metastases from the site of origin has occurred. Some modest improvement in survival has been shown in a trial of terminally ill patients with oat cell carcinoma with the drug warfarin which inhibits clotting (26). One problem with such drugs is that complete inhibition is never achieved because of very real risks of major haemorrhage. Inhibition of the fibrin E stimulatory contribution not to tumour growth but to tumour angiogenesis may be a useful adjunct to the current partially effective treatments by chemotherapy and radiotherapy. Other tumour cells which may be used as a target include cells of solid tumours such as lung (including small cell lung), bowel (colon), breast, ovarian, prostate, stomach, liver, pancreatic and skin tumours, as well as leukaemias.

Fibrin Glues for Surgery: Modification of fibrin glues to promote or inhibit the cell proliferation induced by the fibrin degradation products can be achieved by preparation and admixture with promoters or inhibitors of the site of interaction of fibrin E as provided by the present invention. These glues are increasingly used for a wide variety of operations where sutures are impractical.

In all these examples of disease, the clinical aim would be to prevent the initiating cause but this is often not possible. Selective inhibition of angiogenesis and cell proliferation would be highly desirable. At the same time, it would be preferable to avoid interference with other aspects of the normal inflammatory response, and with blood clotting and fibrinolysis.

However clinical manipulation at one site may conflict with clinical problems at other sites. For example, systemic administration of an antiangiogenic drug to inhibit tumour growth may adversely affect normal healing and repair of a healing skin wound, or a peptic ulcer of stomach.

The severity of potential limitations depends on the therapeutic margin of treatment success over unwanted side effects. Short term treatment and localised treatment offer solutions to some problems but not all. It is therefore envisaged to utilise protective or therapeutic treatments at the other sites and conditions at risk of collateral damage. herefore, treatments may be developed whereby cell proliferation and/or angiogenesis inhibitors may be used at the site of interest or systemically but locally protective FDP induced cell proliferation and/or angiogenesis agonists are provided at other sites that stimulate angiogenesis and the normal cell proliferative response. Combinations of systemic and local administration may become feasible and effective.

In general, the methods will involve administering to a patient in need of treatment an effective amount of a peptide, analog or antibody (or composition thereof) of the invention. Suitable routes of administration of compounds of the invention include oral or parenteral, and will depend in part upon the intended use and the discretion of the physician. Small peptides may be administered orally although parenteral administration may generally be more convenient in some circumstances.

The amount of peptides, analogs or antibodies of the invention administered to a patient is ultimately at the discretion of the physician, taking account of the condition of the patient and the condition to be treated.

Doses may be administered continuously, e.g in the form of a drip, or at discrete intervals, e.g twice daily, daily, weekly or monthly. Doses may also be administered topically to achieve concentrations of active agent on the skin in the ranges described above.

Where a peptide, analog or antibody of the invention is to be administered in conjunction with a cytotoxic or cytostatic agent, the dose of said agent will be in accordance with manufacturers' instructions.

Peptide, analogs or antibodies may be selectively directed to tumour cells by various mechanisms in order to enhance their effectiveness and to avoid effects on normal cells. Such mechanisms include coupling the peptide, analog or antibody to molecules which specifically interact with receptors or antigens on target cells, such as VEGF receptors or CEA. Alternatively gene therapy vectors expression peptides of the invention may comprise an expression system whose promoter is selectively activated in tumour cells, such as promoters active in fetal liver cells.

In a further embodiment, a peptide, analog or antibody of the invention may be incorporated into a stent which is introduced into the arteries of a patient during an angioplasty procedure. This is in order for the peptide, analog or antibody of the invention to treat restenosis. The stent is a hollow metal tube, usually made of stainless steel and optionally coated with a polymeric material such as a plastic which is expanded during the procedure so as to be left in place in the artery to treat heart disease caused by arterial narrowing. A problem with this procedure is the occurrence of restenosis, i.e. the cardiovascular cells tend to grow back and further treatment is ultimately required. By coating the stent with a peptide, analog or antibody of the invention, the peptide, analog or antibody is delivered locally into the cardiovascular tissue and will prevent local regrowth of cells by inhibiting stimulation of cell proliferation by FDPs.

Peptides, analogs or antibodies of the invention may be either coated onto or incorporated into the stent by conventional means known per se in the art. For example, the peptides, analogs or antibodies may be mixed with a pharmaceutically acceptable carrier compatible with the stent material and coated on or into the stent. Where incorporation into the stent is contemplated it is desirable that the stent comprises an open celled polymeric structure. Where the stent is in the form of a mesh, the peptides, analogs or antibodies may be incorporated into a suitable delayed release carrier contained in the spaces between the mesh strands. Delayed release formulations are widely available for a number of different purposes in the art; these include formulations based on pharmaceutically acceptable polymers which dissolve slowly in the body following implantation.

A number of coronary stents have been approved for clinical use in the USA by the FDA. These include balloon expandable stents such as the Palmaz-Schatz stent made by Cordis Corporation (a division of Johnson & Johnson Interventional Systems) and the Gianturco-Roubin II (GR-II) stent made by Cook Cardiology (Bloomington, Ind., USA). Self-expanding stents are also used in the art, e.g. the Wallstent (Medinvent-Schneider, Switzerland). Generally these stents are made of a wire of around 0.1 mm (e.g. from 0.07 to 1.5 mm) diameter, are designed to expand to a diameter of 3–5 mm, and are around 10 to 20 mm in length.

Examples of stent coatings to which reference may be made for the provision of peptide coated stents of the invention include a heparin-coated Palmaz-Schatz stent (Serruys et al, Circulation, 1996, 93;412–422) and a platelet glycoprotein IIa/IIIa receptor antibody polymer-coated stent (Aggarwal et al. Circulation, 1996, 94; 3311–3317).

For further guidance, those of skill in the art may also make reference to "Coronary Artery Stents", an ACC Expert Consensus Document (Pepine et al, J. Am. Coll. Cardiol., 1996, 28; 782–794.

The following examples illustrate the invention.

DESCRIPTION OF THE DRAWINGS

FIG. 1 illustrates the effect of admixture of 3 different rabbit anti phage antibodies with stimulatory FDP.

FIG. 2 illustrates the effect of admixture of anti phage antibodies against selected phage clones 42, 43 and 44 to abolish the stimulatory effect of FDP. Student's t test on log transformed data shows a significant (P<0.05) increase in DNA synthesis compared with the buffer only control group by FDP. The 3 anti phage groups are significantly different from the FDP group, but not from the control group.

EXAMPLES OF THE INVENTION

Example 1

Figure 3:
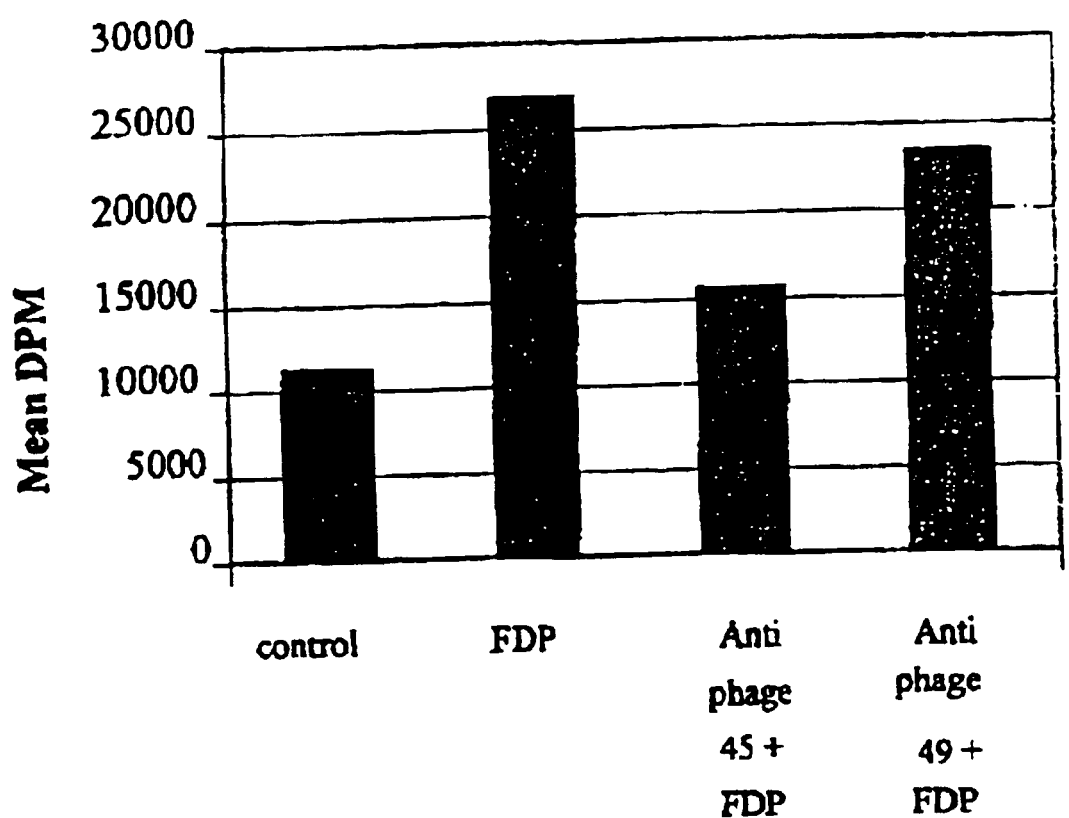
FIG. 3 illustrates the effect of admixture of anti phage antibodies. against selected phage clones 45 and 49 with stimulatory FDP. The stimulatory effect of FDP was inhibited by anti phage 45 (P<0.05) but not with anti phage 49.

Fibrin Fragment E Binds to a 66 kDa Cell Membrane Component i) Digoxygenin Labelling of Fibrin Fragment E 327 mg of digoxygenin ester, dissolved in 8.18 ml DMSO was added to 1 mg of fibrin fragment E in 1 ml of phosphate buffered saline (PBS) and incubated at room temperature for 2 hours. This was then dialysed against PBS (3 changes of 11) to remove the unreacted ester and DMSO. Detection of the labelled protein was then carried out using anti-digoxygenin alkaline phosphatase raised in sheep (Boehringer).

ii) Ligand Blot

Chick fibroblasts, Cos7, mouse 3T3 and human embryonic lung cells (HEL) were cultured in a 25 cm² flask (Nunc) until confluent (approximately 3×10⁶ cells). The cells were then floated off the flask using PBS with 2% EDTA and slight scrapping with a rubber policeman. The cells were centrifuged for 5 min at 3,000 rpm and resuspended in hypotonic shock solution, sonicated for 30 min and then centrifuged and resuspended in 1 ml of PBS. 100 ml of the cells was then added to 35 ml of SDS containing gel loading dye (8% SDS, 40% glycerol, 12.5% 0.5M Tris-glycine buffer pH 6.8 and 10 mg of bromophenol blue), and heated to 95° C. for 5 min.

50 ml of the cells in loading dye were applied to gradient polyacrylamide gels (3–20%) and electrophoresed for 5 hours until the dye reached the base of the gel. The gel was then washed several times in Tris buffered saline containing 0.5% Triton X-100 to remove the SDS. The gel was then blotted on to PVDF membrane (Millipore) using a Bio-Rad blotting system in Tris glycine buffer (25 mM Tris and 192 mM glycine).

The blotting membrane was blocked using 5% bovine serum albumin in Tris buffered saline (TBS). The blot was then incubated overnight at 37° C. with digoxygenin labelled fibrin fragment E (100 mg in 100 ml of TBS). The membranes were washed three times in TBS 0.5% Tween 20 for 10 minutes and incubated for 1 hour with sheep anti-digoxygenin antibody conjugated to alkaline phosphatase. The membrane was washed, 3 times, again with TBS Tween followed by development with nitro blue tetrazolium, bromo-chloro-indolyl-phosphate in sodium bicarbonate buffer (NaHCO₃, 100 mM, MgCl₂ 10 mM) to visualise the position of the receptor containing band. For each cell type, a band was identified of approximately 66 kDa. To confirm this finding, membrane immunoblot experiments were performed using cells previously challenged with fibrin fragment E as described below.

iii) Membrane Immunoblotting

Chick fibroblasts, Cos7, mouse 3T3 and human embryonic lung cells (HEL) were cultured in a 25 cm² flask (Nunc) until confluent (approximately 3×10⁶ cells). 100 mg of digoxygenin labelled fibrin fragment E was added to the cells and incubated at 37° C. Cells were harvested by rinsing with PBS and then floated off the flask using PBS with 2% EDTA and slight scraping with a rubber policeman. The cells were centrifuged for 5 min at 3,000 rpm and resuspended in hypotonic shock solution for 15 min, centrifuged and resuspended in 1 ml of PBS. 100 ml of the cells was then added to 35 ml of SDS containing gel loading dye (8% SDS, 40% glycerol, 12.5% 0.5M Tris glycine buffer, pH 6.8 and 10 mg of bromophenol blue), and heated to 95°C. for 5 min.

50 ml of the cells in loading dye were applied to gradient polyacrylamide gels (3–20%) and electrophoresed for 5 hours until the dye reached the base of the gel. The gel was then washed several times in Tris buffered saline containing 0.5% Triton X to remove the SDS. The gel was then blotted on to PVDF membrane (Millipore) using a Bio-Rad blotting system in Tris glycine buffer (25 mM Tris and 192 mM glycine).

The blotting membrane was blocked using 5% bovine serum albumin in Tris buffered saline (TBS). The blot was then incubated overnight at 37° C. for 1 hour with rabbit anti fibrinogen antibody (Dako). The membranes were washed three times in TBS 0.5% Tween 20 for 10 minutes and incubated for 1 hour with goat anti rabbit antibody conjugated to alkaline phosphatase. The membrane was washed, 3 times, again with TBS Tween followed by development with nitro blue tetrazolium (NBT), bromo-chloro-indolyl-phosphate (BCIP) in sodium bicarbonate buffer (NaHCO₃ 100 mM, MgCl₂ 10 mM pH 9.8). This resulted in a band of approximately 122 kD, which is consistent with fragment E (55 kD) bound to a membrane fragment of 66 kD. Further evidence of binding to a receptor iv) Cell Immunohistochemistry Chick fibroblasts were cultured in a 25 cm² flask (Nunc) until confluent (approximately 3×10⁶ cells). The cells were washed in PBS and then trypsinised and diluted to 3×10⁵ cells per ml in Dulbecco modified medium with 10% foetal calf serum. 50 ml of the cells suspension was plated into each well of a Nunc culture well slide. The cells were incubated overnight to allow adhesion and recovery from the passaging. Digoxygenin labelled fibrin fragment E was added to a final concentration of 8 mg per ml. Control wells contained unconjugated digoxygenin and PBS.

The cells were rinsed after 2 hours with PBS then washed 3 times in TBS followed by one wash in distilled water. The cells were then incubated for 2 hours with sheep anti-digoxygenin alkaline phosphatase. The slides were then washed three times in TBS and developed with NBT and BCIP in bicarbonate buffer pH 9.8. The slides were air dried and then mounted for observation of membrane staining under the microscope. The cells were shown to bind fibrin fragment E.

v) Cell Binding Assays

Chick fibroblasts, Cos7, mouse 3T3 and human embryonic lung cells (HEL) were cultured in a 25 cm² flask (Nunc) until confluent (approximately 3×10⁶ cells). The cells were trypsinised and resuspended at concentration of 1.3×10⁵ cells/ml. 200 µl of this cell suspension was added to each well of a 96 well culture plate (Nunc). The cells were incubated overnight at 37° C. to allow adherence and recovery. The cells were then divided into three sections, digoxygenin controls, PBS controls and digoxygenin labelled fragment E tests. Increasing concentrations of digoxygenin and digoxygenin labelled fibrin fragment E were applied from 0–30 mg per well. The plates were incubated for 6 hours at 37° C. under culture conditions.

The plates were emptied of media and washed three times with PBS. The cells were then incubated for 2 hours with sheep antidigoxygenin alkaline phosphatase and developed with p-nitrophenyl phosphate in bicarbonate buffer pH 9.8. The plates were read on a Titertek Multiscan plate reader at 405 nm. For each of the cell types, high absorbance was demonstrated compared to the control preparations, indicating binding of the digoxygenin labelled fibrin fragment E to the cells.

The demonstration that fibrin fragment E binds to each of the cell types tested suggests that a fibrin fragment E specific receptor of 66 kDa is present on the cell membrane.

Example 2

Antibodies to Fibrin Fragment E Block FDP Induced Stimulation of Cell Proliferation i) Polyclonal Antibody Production Polyclonal antibodies were raised to fibrin fragment E using the following immunisation protocol.

Rabbits and rats were immunised with fibrin fragment E, made by thrombin treatment of fibrinogen fragment E (Diagnostica Stago). 50 mg of fibrin fragment E in 0.5 ml of PBS was mixed with 0.5 ml of Freunds complete adjuvant. The rabbits were immunised intramuscular and the rats intraperitoneal. The animals were then boosted at 4 and 8 weeks later with 50 mg of a long fibrin digest, which was shown to contain only fibrin fragment E, in incomplete Preunds adjuvant. The animals were then bled and the antisera tested for reactivity on blots of fibrin degradation products.

ii) CAM Cell Proliferation Assay

Cell proliferation was measured using the chick chorio-allantoic membrane (CAM) model as described previously (4, 29, 30). The assay used is based on quantitative measurement of DNA synthesis in the CAM after exposure to control and test substances 18 h after application in liquid form to the whole "dropped" area of each CAM (4, 29). This assay is a measure of changes in CAM vascularity (30).

The rabbit and rat antisera were mixed with active fibrin degradation products. These were applied to the chick CAM with a positive control (fibrin degradation products) and a negative control (the antibody alone). The CAM was processed for incorporation of tritiated thymidine. Results showed that the fibrin degradation products were active and that the rat and rabbit antisera to fibrin fragment E removed the activity.

Example 3

Identification of Peptides

The inventors have screened a peptide library made in Fd phage using polyclonal antisera capable of blocking activity of fibrin fragment E.

i) The Phage Library

Rat and rabbit polyclonal antibodies were raised against purified human fibrin fragment E as described previously (4). All secondary antibodies were purchased from commercial sources (Sigma Chemicals). A sample of the 2×108 clone 15 amino acid peptide gene VIII library as described by Scott & Smith (1990) (27), was obtained as a phage suspension from George Smith (University of Missouri Columbia, USA). 20 ml of this phage suspension was infected into mid-log K91 cells, which were IPTG induced when the OD reached approximately 0.9 resulting in the formation of 6.6×109 tetracycline-resistant transductants. These were amplified by growth in one litre of 2×TY medium containing 20 mg tetracycline/ml for 24 hours at 37° C. with shaking.

Before precipitation of the phage, the cultures were first spun for 10 minutes at 8,000 RPM at 4° C. to remove bacteria. The supernatant was kept, and PEG 6000 20% (w/v), 0.5 molar NaCl, added resulting in a final PEG concentration of ~4% (w/v). The cultures were then cooled on ice for 1 hour and centrifuged for 20 minutes at 10,000 RPM at 4° C. The phage were resuspended in 10 ml of Tris buffered saline.

ii) Selection of Phage

Selection of phage from the library was carried out using a procedure based on the biopanning method of Parmley & Smith (1988) (9). 1 ml of each polyclonal antibody in PBS at dilutions from 1:200 to 1:1,000 was added to a 60 mm petri dish (Nunc) and incubated in an orbital incubator at room temperature overnight to allow antibody adhesion. The next day 5 mls of blocking solution (PBS, 0.5% Tween, 5% skimmed milk), was added to each dish, in order to block any sites not adhered to by the polyclonals. The dishes were then left to incubate in an orbital incubator for 1 hour at room temperature, and then washed 5 times in PBST (PBS, 0.5% Tween).

100 μl of the gene VIII library was added to each dish, and the dishes incubated at room temperature for 1 hour, in an orbital incubator. The unattached phage were then poured away and the dishes washed 5 times in PBS-Tween. Phage which remained bound to the immobilised polyclonals were recovered from the antibodies by the addition of 800 μl 0.1 M HCl (pH. 2.2 with glycine), and allowed to incubate at room temperature for 15 minutes. 48 μl of unbuffered 2 M Tris base was then added to each dish to neutralise the acid.

For round 1 biopanning, the contents of each dish were added to 3 ml cultures of mid-log $E.\ coli$ K91, and allowed to incubate at room temperature for 10 minutes. 12 ml of LB medium (10 g Tryptone, 5 g yeast extract, 10 g NaCl in 1 litre $H_2O$, pH 7.5) was then added to each culture. Tetracycline was also added to a concentration of 0.2 mg/ml, and the cultures incubated at 37° C. (225 RPM) for 40 minutes. Additional tetracycline was then added, to a final concentration of 20 mg/ml and the cultures allowed to grow for 16–20 hours at 37° C. (225 RPM). Phage input and output titres were determined by a plating and incubation on LB agar dishes.

A second round of amplification was carried out as for the first, except that 100 μl of phage recovered from the first rounds of biopanning was used against the blocked polyclonals. A third round of biopanning was also carried out except that 100 μl of phage recovered from the second round of biopanning was used against the blocked polyclonals.

During rounds 2 & 3 negative controls, consisting of K91 cells, with no added phage, were used to demonstrate that the K91 stocks had not acquired tetracycline resistance by another means i.e. plasmid transfer. A fourth round of amplification was carried out as for the third except that 100 μl of phage recovered from the second round of biopanning was used against polyclonals from a different species, i.e. phage recovered after three rounds of biopanning against the rabbit polyclonals, was used against the rat polyclonals, and phage recovered after three rounds of biopanning against the rat polyclonals was used against the rabbit polyclonals. This was to demonstrate the homogeneity of different polyclonals raised in two different species against the same antigen and to reject non shared target epitopes.

iii) Testing of Reactive Clones

Reactive clones were identified from the output of round 4 with an ELISA using a 1:200 dilution of rat anti fibrin E polyclonal for coating one set of wells, and the second coated with a 1:200 dilution of rabbit anti fibrin E polyclonal. Samples of the selected phage clones were each run on PAGE and immunoblotted with the existing anti E antisera that were the basis of the selection process. The 60 selected reactive clones were combined into 3 groups, 1–20, 21–40, and 41–60, and samples mixed with Preund's complete adjuvant and used to immunise rats and rabbits. The resultant new antisera were tested initially by immunoblotting of PAGE of selected phage clone proteins and also human FDP. Polyclonal antisera raised against 21 to 40, and 41 to 60 detect fragment E bands on immunoblots. In contrast, polyclonal antisera raised against 1 to 20 do not.

The rabbit antisera were then tested for ability to block the stimulatory activity of human FDP on the chick CAM model. The assay used was based on quantitative measurement of DNA synthesis in the CAM after exposure to control and test substances 18 h after application in liquid form to the whole "dropped" area of each CAM (4,29). This assay is a measure of changes in CAM vascularity (30). Anti phage antisera, raised by relatively short term immunisation of rabbits, were used at a 1/2 dilution and admixed with FDP used at a concentration of approximately 1.95 mg/ml diluted before use to 1/10. Controls included buffer only and antiserum only groups of CAMs. After filter sterilisation, 0.3 ml was added onto each CAM dropped surface.

iv) Demonstration of Blocking of FDP Angiogenic Activity

FIG. 1 illustrates one experiment where rabbit anti phage 1–20 does not appear to block the stimulatory effect of FDP after admixture, but rabbit anti phage 21–40 and 41–60 do inhibit the stimulation. Repeat experiments have now been completed a further 2 times for the latter two antibodies with similar inhibition. Antibody alone and buffer alone controls have no effect.

v) Testing of Individual Clones

Antibodies raised against individual clones 41–60 were tested for inhibitory activity using the chick CAM assay. Antibodies raised against clones 42, 43, 44 and 45 were found to be inhibitory (FIGS. 2, 3). In contrast, antibodies to clones 49 (FIG. 3) and 53, for example, were not inhibitory.

vii) Sequencing of Individual Peptides

Amino acid sequences were obtained for clones 45 and 49. Peptides recognised by clone 45 antiserum were obtained by re-screening the phage library. The following four peptide sequences were obtained for clone 45:

CRAHSFGSPRPLPVV (SEQ ID NO:1)
SRAHSFGSPRPLPVV (SEQ ID NO:2)
CRAHSFVSPRPLPVV (SEQ ID NO:3)
QPDPHLMMWKLPGFP (SEQ ID NO:4)

A single sequence was obtained for clone 49
ALSKRPVGRPRVCTG (SEQ ID NO:5)

Figure 4:
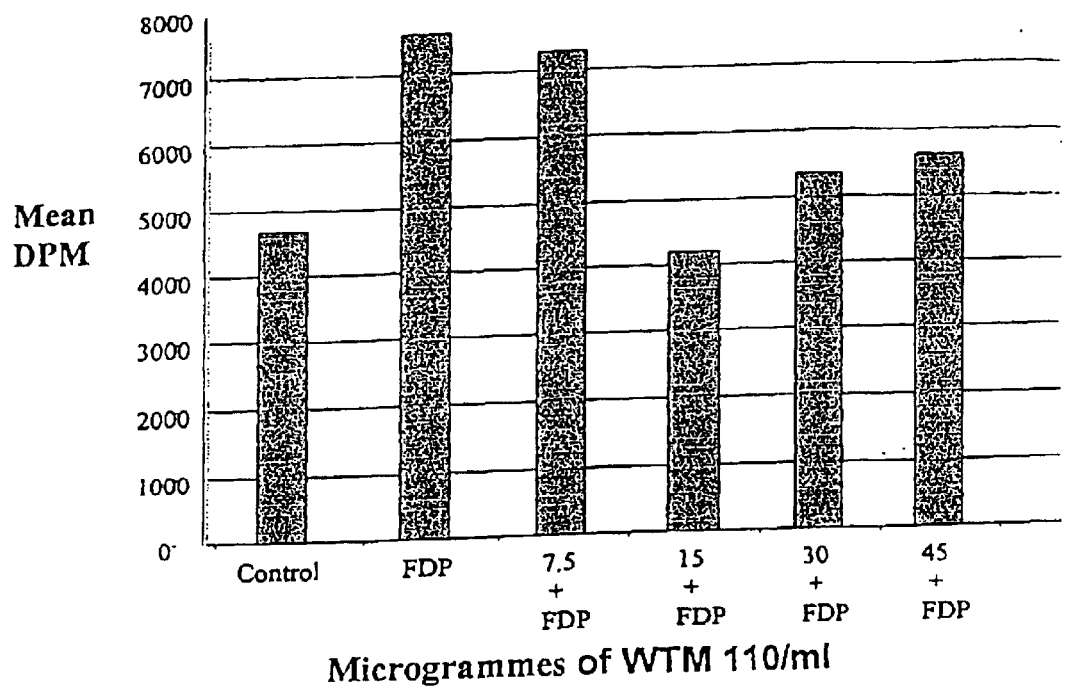
FIG. 4 illustrates that peptide WTM110 inhibits the stimulatory effect of FDP.

Example 4 i) Peptides Corresponding to the Amino Acid Sequences of Clone 45 Inhibit Cell Proliferation The peptide corresponding to SEQ ID NO:1 was synthesised and named WTM110. WTM110 was tested for modulation of FDP induced cell stimulation using the chick CAM assay as described above. The results are shown in FIG. 4. At 7.5 µg/ml, there is little inhibition of cell proliferation. However, when the concentration was increased to 15 µg/ml, inhibition was demonstrated with cell proliferation reduced to control level.

ii) Antibody Raised to WTM110 Inhibits Cell Proliferation

Figure 5:
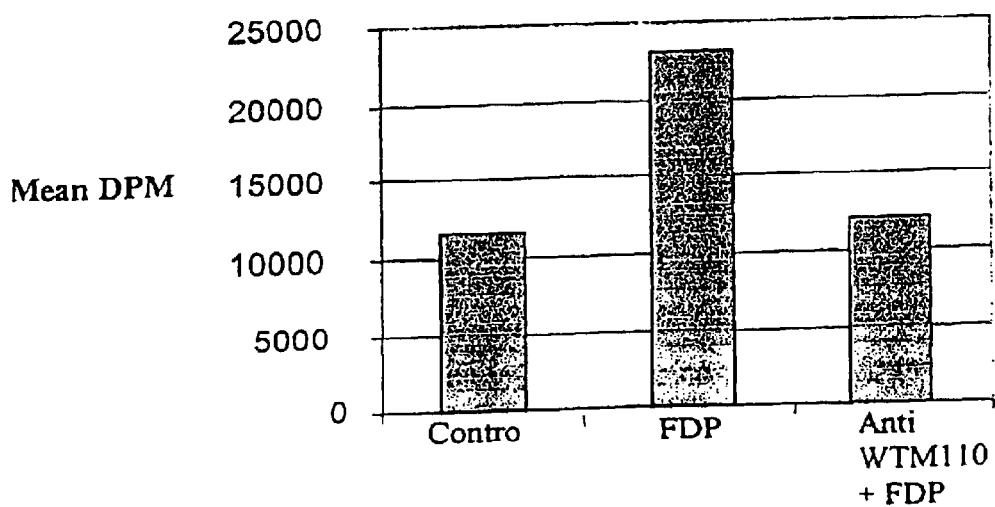
FIG. 5 illustrates that antibody raised to WTM abolishes the stimulatory effect of FDP.

An antibody was raised to WTM110 and used in the chick CAM assay as described above. As shown in FIG. 5, in the presence of anti-WTM110 antiserum, stimulation of cell proliferation by FDPs was inhibited.

The sequence information for the finally selected epitopes, derived from analysis of each phage clone DNA insert, can be used not only to locate the active site on the molecule, and to perpetuate blocking antibodies, but also to synthesise large quantities of short peptides and short peptide analogues. These can be tested for competitive blocking activity for human fragment E. Such peptides and analogs are potential therapeutic agents in the longer term for blocking the cell stimulatory effects of fibrin fragment E in vivo in a potentially wide variety of pathologies (30) without the attendant risks of interfering in clotting or fibrinolysis. Our previous work has shown that admixture of blocking antisera to fibrin E will inhibit the angiogenic effect of experimental mouse wound extracts (31) and extracts of proliferative types of human atherosclerotic plaques (21). We have not yet attempted inhibition in vivo. Sustained delivery in vivo to inhibit, for example, wound healing should be more readily achieved by administration of small peptides than polyclonal antisera from another species.

The sequence information for the finally selected epitopes, derived from analysis of each phage clone DNA insert, has been used to locate parts of the active site on the molecule. The sequence information can also be used to synthesise large quantities of short peptides. These can be tested for competitive blocking activity for human fragment E. Such peptides are potential therapeutic agents.

Knowledge of the location of the active site, even though limited to a few short segments of the protein molecule, allows further exploration of non-immunogenic adjacent areas, within the known molecular structure of fibrin E, which may influence biological activity. Synthetic peptides and analogs of such regions are likely to provide further experimental agents that are potential drugs.

References

1 McKenzie R. Pepper D S, Kay A B. The generation of chemotactic activity for human leucocytes by the action of plasmin on human fibrinogen. Thromb Res 1975; 6: 1–8.

2 Thompson W D, Campbell R. Evans A T. Fibrin degradation and angiogenesis: quantitative analysis of the angiogenic response in the chick chorioallantoic membrane. J Pathol 1985; 145: 27–37.

3 Thompson W D, Evans A T, Campbell R. The control of fibrogenesis; stimulation and suppression of collagen synthesis in the chick chorioallantoic membrane with fibrin degradation products, wound extracts and proteases. J Pathol 1986; 148: 207–215.

4 Thompson W D, Smith E B, Stirk C M, Marshall F I, Stout A J, Kocchar A. Angiogenic activity of fibrin degradation products is located in fibrin fragment E. J Pathol 1992; 168: 47–53.

5 Romer J., et al. Impaired wound healing in mice with a disrupted plasminogen gene. Nature Med. 2, 287–292 C1996)

6 Bugge T H, Kombrinck K W, Flick M J, Daugherty C C, Danton M J, Degen J L. Loss of fibrinogen rescues mice from the pleiotropic effects of plasminogen deficiency. Cell 1996; 87: 709–19.

7 Thompson W D, Harvey J A, Kazmi M A, Stout A J. Fibrinolysis and angiogenesis in wound healing. J Pathol 1991; 165: 311–318.

9 Thompson W D, McNally S J, Ganesalingam N, McCallion D S E, Stirk C M, Melvin W T. Wound healing, fibrin and angiogenesis. In: Molecular, Cellular and Clinical Aspects of Angiogenesis. Ed M Maragoudakis, Plenum Press, New York, 1996. pp 161–172

9 Sarembock I J, Gertz S D, Gimple L W, Owen R M, Powers E R, Roberts W C. Effectiveness of recombinant desulphatohirudin in reducing restenosis after balloon angioplasty of atherosclerotic femoral arteries in rabbits. Circulation 1991; 84, 232–243

10 Schwartz S M. Serum-derived growth factor is thrombin? J Clin Invest 1993; 91: 4

11 Darrow A L, Fung-Leung W P, Ye R D, Santulli R J, Cheung W M, Derian C K, Burns C L, Damiano B P, Zhou L, Keenan C M, Peterson P A, Andrade-Gordon P R. Biological consequences of thrombin receptor deficiency in mice. Thromb Haemost 1996; 76: 860–866.

12 Herbert J M, Guy A F, Lamarche I, Mares A M, Savi P, Dol F. Intimal hyperplasia following vascular injury is not inhibited by an antisense thrombin receptor oligodeoxy-nucleotide. J Cell Physiol 1997; 170: 106–114.

13 Naito M, Sabally K, Thompson W D, Stirk C M, Smith E B, Benjamin N. Stimulation of proliferation of smooth muscle cells in culture by fibrin degradation products. Fibrinolysis 1996; 10 (Suppl 4): 1–26.

14 Woodward M, Lowe G D O, Rumley A, Tunstall-Pedo H. Fibrinogen as a risk factor for coronary heart disease and mortality in middle-aged men and women. Eur Heart J 1998; 19: 55–62.
15 Lowe G D O, Yarnell J W G, Sweetnam P M, Rumley A, Thomas H F. Fibrin D-dimer, tissue plasminogen activator, plasminogen activator inhibitor, and the risk of major ischaemic heart disease in the Caerphilly study. Thromb Haemost 1998; 79: 129–133.
16 Lip G Y H, Lowe G D O. Fibrin D-dimer: a useful clinical marker of thrombogenesis. Clin Sci 1995; 89: 205–214.
17 Tschopl M, Tsakiris D A, Marbet G A, Labs K-H, Jager K. Role of hemostatic risk factors for restenosis in peripheral arterial occlusive disease after transluminal angioplasty. Arterioscler Thromb Vasc Biol 1997; 17: 3208–3214.
18 Smith E B, Keen G A, Grant A, Stirk C. Fate of fibrinogen in human arterial intima. Atherosclerosis 10, 263–275, 1990.
19 Duguid J B. Thrombosis as a factor in the pathogenesis of coronary atherosclerosis. J Path Bact 1946; 58: 207–212.
20 Thompson W D, McGuigan C J, Snyder C, Keen G A, Smith E B. Mitogenic activity in human atherosclerotic lesions. Atherosclerosis 1987; 66: 85–93.
21 Thompson W D, McGuigan C J, Snyder C, Keen G A, Smith E B. Mitogenic activity in human atherosclerotic lesions. Atherosclerosis 1987; 66: 85–93.
22 C M Stirk, A Kochhar, E B Smith, W D Thompson. Presence of growth-stimulating fibrin degradation products containing fragment E in human atherosclerotic plaques. Atherosclerosis 1993; 103: 159–169.
23 Dvorak H F, Nagy J A, Berse B, Brown L F, Yeo K T, Dvorak A M, van de Water L, Sioussat T M, Senger D R. Vascular permeability factor, fibrin, and the pathogenesis of tumor stroma formation. Ann N Y Acad Sci 1992; 667: 101–111.
24 Zacharski L R, Schned A R, Sorenson G D. Occurrence of fibrin and tissue factor antigen in human small cell carcinoma of the lung. Cancer Res 1983; 43: 3963–3968.
25 Zacharski L R, Memoli V A, Rousseau S M. Coagulation-cancer interaction in situ in renal cell carcinoma. Blood 1986; 68:394–399.
26 Rickles F R, Hancock W W, Edwards R L, Zacharski L R. Antimetastatic agents. I. Role of cellular procoagulants in the pathogenesis of fibrin deposition in cancer and the use of anticoagulants and/or antiplatelet drugs in cancer treatment. Semin Thromb Hemost 1988; 14: 88–94.
27 Scott J K, and Smith G P. Searching for peptide ligands with an epitope library. Science 1990; 249: 186–390.
28 Parmley S F, and Smith G P. Antibody-selectable filamentous Fd phage vectors affinity purification of target genes. Gene 1988; 73: 305–318.
29 Thompson W D, Smith E B, Stirk C M, Wang J. Fibrin degradation products in growth stimulatory extracts of pathological lesions. Blood Coagulation and Fibrinolysis 1993; 4: 113–116.
30 Thompson W D, Brown F I. Measurement of angiogenesis: mode of action of histamine in the chick chorioallantoic membrane is indirect. Int J Microcirc 1987; 6: 343–357.
31 Thompson W D, McNally S J, Ganesalingam N, McCallion D S E, Stirk C M, Melvin W T. Wound healing, fibrin and angiogenesis. In: Molecular, Cellular and Clinical Aspects of Angiogenesis. Ed M Maragoudakis, Plenum Press, New York, 1996. pp 161–172.
32 Thompson W D, Stirk C M, Keating A J, Reid A, Smith E B, Melvin W T. Fibrin degradative pathways in healing, atherosclerosis and tumour invasion. In: Angiogenesis: Models, Modulators and Clinical Applications. Ed M Maragoudakis. Plenum Press, New York, 1998 pp 233–240.

What is claimed is:

1. A peptide consisting of an amino acid sequence selected from the group consisting of:

CRAHSFGSPRPLPVV (SEQ ID NO:1),

SRAHSFGSPRPLPVV (SRQ ID NO:2), and

CRAHSFVSPRPLPVV (SEQ ID NO:3)

said peptide being effective to bind a fibrin fragment E binding site, thereby stimulating fibrin fragment E activity.

2. A peptide according to claim 1, wherein said activity is stimulation of cell proliferation or angiogenesis.

3. A composition comprising a peptide according to claim 1 in association with a pharmaceutically acceptable carrier or diluent.

* * * * *